(12) United States Patent
Madsen et al.

(10) Patent No.: US 8,879,073 B2
(45) Date of Patent: Nov. 4, 2014

(54) OPTICAL METROLOGY USING TARGETS WITH FIELD ENHANCEMENT ELEMENTS

(71) Applicant: KLA-Tencor Corporation, Milpitas, CA (US)

(72) Inventors: Jonathan M. Madsen, Los Altos, CA (US); Andrei V. Shchegrov, Campbell, CA (US); Michael Bakeman, San Jose, CA (US); Thaddeus Gerard Dziura, San Jose, CA (US); Alexander Kuznetsov, Mountain View, CA (US); Bin-Ming (Benjamin) Tsai, Saratoga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 69 days.

(21) Appl. No.: 13/770,202

(22) Filed: Feb. 19, 2013

(65) Prior Publication Data
US 2013/0222795 A1     Aug. 29, 2013

Related U.S. Application Data

(60) Provisional application No. 61/603,187, filed on Feb. 24, 2012.

(51) Int. Cl.
*G01B 11/14* (2006.01)
*G01B 11/06* (2006.01)
*G01N 21/956* (2006.01)

(52) U.S. Cl.
CPC .......... *G01N 21/956* (2013.01); *G01B 11/0641* (2013.01); *G01B 11/0625* (2013.01)
USPC ............................. 356/625; 356/630; 356/446

(58) Field of Classification Search
CPC ............ G01N 21/956; G01N 21/4788; G01N 2021/213; G01B 11/0625; G01B 11/0641; G01B 11/02; G01B 2210/56
USPC .......................... 356/445–448, 625, 630–632
See application file for complete search history.

(56) References Cited

U.S. PATENT DOCUMENTS

| | | |
|---|---|---|
| 4,999,014 A | 3/1991 | Gold et al. |
| 5,181,080 A | 1/1993 | Fanton et al. |
| 5,877,859 A | 3/1999 | Aspnes et al. |

(Continued)

OTHER PUBLICATIONS

International Search Report and Written Opinion mailed on Jun. 11, 2013, for PCT Application No. PCT/US2013/027180 filed on Feb. 21, 2013, by KLA-Tencor Corporation, 10 pages.

*Primary Examiner* — Hoa Pham
(74) *Attorney, Agent, or Firm* — Spano Law Group; Joseph S. Spano

(57) ABSTRACT

Methods and systems for enhancing metrology sensitivity to particular parameters of interest are presented. Field enhancement elements (FEEs) are constructed as part of a specimen to enhance the measurement sensitivity of structures of interest present on the specimen. The design of the FEEs takes into account measurement goals and manufacturing design rules to make target fabrication compatible with the overall device fabrication process. Measurement of opaque materials, high-aspect ratio structures, structures with low-sensitivity, or mutually correlated parameters is enhanced by the addition of FEEs. Exemplary measurements include critical dimension, film thickness, film composition, and optical scatterometry overlay. In some examples, a target element includes different FEEs to improve the measurement of different structures of interest. In other examples, different target elements include different FEEs. In some other examples, field enhancement elements are shaped to concentrate an electric field in a thin film deposited over the FEE.

20 Claims, 12 Drawing Sheets

(56) References Cited

U.S. PATENT DOCUMENTS

| | | |
|---|---|---|
| 6,239,876 B1 * | 5/2001 | Brandenberg .................. 356/481 |
| 7,478,019 B2 | 1/2009 | Zangooie et al. |
| 7,567,351 B2 | 7/2009 | Opsal et al. |
| 8,068,228 B2 | 11/2011 | Feng |
| 2003/0011786 A1 * | 1/2003 | Levy et al. .................... 356/600 |
| 2007/0201043 A1 * | 8/2007 | Raymond ...................... 356/625 |
| 2009/0040613 A1 * | 2/2009 | Feng ............................. 359/558 |
| 2011/0233648 A1 | 9/2011 | Seol et al. |

* cited by examiner

OPTICAL METROLOGY USING TARGETS WITH FIELD ENHANCEMENT ELEMENTS

CROSS REFERENCE TO RELATED APPLICATION

The present application for patent claims priority under 35 U.S.C. §119 from U.S. provisional patent application Ser. No. 61/603,187, entitled "Optical Metrology Using Targets With Field Enhancement Elements," filed Feb. 24, 2012, the subject matter of which is incorporated herein by reference.

TECHNICAL FIELD

The described embodiments relate to optical metrology and inspection systems and methods, and more particularly to optical metrology and inspection scenarios involving targets designed to improve measurement results.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes based on optical metrology are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures. Traditionally, optical metrology measurements are performed on targets consisting of thin films and/or repeated periodic structures. These films and periodic structures typically represent the actual device geometry and material structure or an intermediate design during device fabrication.

As devices (e.g., logic and memory devices) move to ever smaller nanometer-scale dimensions and become more complex in terms of their three-dimensional geometry and selection of materials, characterization of such devices increases in difficulty. For example, high aspect ratio, three dimensional structures (e.g., some memory structures) present a particular challenge to optical metrology. Often, high aspect ratio geometry physically impedes the exposure of bottom layers to optical radiation. Hence, measurement sensitivity suffers due to low electromagnetic field intensity in the areas of interest. In another example, material opacity (e.g., increasingly used high-k materials) impedes the penetration of optical radiation to bottom layers. The lack of exposure to optical radiation dramatically reduces the measurement sensitivity. Furthermore, the lack of measurement data decreases the reliability of the decoupling of correlations among the many parameters characterizing complex structures (e.g., Fin-FETs). Thus, measurement of current devices with optical metrology tools (e.g., a spectroscopic ellipsometer or reflectometer) is becoming increasingly challenging.

In response to these challenges, more complex tools that acquire more signals from the target have been employed. For example, more wavelengths (e.g., deep ultraviolet and vacuum ultraviolet wavelengths), more complete information for reflected signals (e.g., measuring multiple Mueller matrix elements in addition to conventional reflectivity or ellipsometric signals), and multiple angles of illumination have been employed. In some examples, a combination of multiple optical inspection systems and non-optical inspection systems have been employed.

However, it has become clear that these approaches cannot reliably overcome fundamental challenges in sensitivity and parameter correlation for many advanced targets, especially those with complex three dimensional structures, opaque materials, or other structures with known, low parameter sensitivity or high parameter correlation. Thus, methods and systems for characterizing devices having complex three dimensional geometry and/or opaque materials at high throughput are desired.

SUMMARY

Methods and systems for enhancing metrology sensitivity to parameters of interest are presented. Field enhancement elements (FEEs) are constructed as part of a specimen to enhance the measurement sensitivity of structures of interest present on the specimen. The design of the FEEs takes into account measurement goals and manufacturing design rules to make target fabrication compatible with the overall device fabrication process. Measurement of opaque materials, high-aspect ratio structures, structures with low-sensitivity, or mutually correlated parameters is enhanced with the addition of FEEs. Exemplary measurements include critical dimension, film thickness, film composition, and optical scatterometry overlay.

In some examples, FEEs directly enhance measurement sensitivity or reduce parameter correlations associated with measurement of a particular target element. In these single target examples the data collected from a single target element (or repeated single target elements) is used to determine measurement parameters. In some other examples, FEEs enhance the measurement sensitivity or reduce parameter correlations associated with measurement of a number of different target elements (i.e., target elements that include differently shaped FEEs) as a part of multi-target optimization.

A variety of types of field enhancement elements may be constructed as part of the process flow for fabricating the device structures of interest. In some examples, the field enhancement provided by FEEs occurs in the areas where FEES are located. For example, a FEE may be a trench or a hole that increases field penetration to lower layers of a device stack. However, in other examples, the field enhancement provided by FEEs occurs in areas of away from the FEE location. For example, a FEE may be a beam steering element, prism element, or wave-guide element that directs the illumination field into an area of interest. In another example, a FEE may be a secondary grating element that couples the illumination field into an area of interest.

In some embodiments, a target element is a single, spatially repeating element (i.e., unit cell) and the target area includes a number of spatially repeated target elements. Hence, a single measurement collects diffracted light from many target elements. In some embodiments, a target element in spatially repeated in one direction. In some other embodiment, the target element is also spatially repeated in another direction, not aligned with the first direction. In this manner, metrology systems have the ability to perform measurements over a target area that includes a number of spatially repeated target elements that generate a grating effect in the output signals that simplifies the subsequent determination of parameters of interest.

In some embodiments, measurement of high-aspect ratio structures of interest is enhanced by employing field enhancement elements to steer or concentrate illumination light into dark recesses of the target element. In this manner penetration of illumination light into the target element is enhanced along with access to vertical layer information.

In some embodiments, measurement of thin film layers is enhanced by employing field enhancement elements such that measurement data can be analyzed to isolate parameters associated with particular layers. For example, film thickness measurements are often complicated by the presence of opaque layers (e.g., metal layers). Similarly, composition measurements are often complicated by low sensitivity to certain measured parameters (e.g., nitrogen percentage). FEEs are introduced into the target area to enhance measurement results by enabling the isolation of the parameters of interest.

In some embodiments, measurements of different parameters of interest are enhanced by a single target element that includes more than one differently shaped FEE. In some other embodiments, different target elements include different FEEs, measurements from which are included in a multi-target analysis.

In some embodiments, a thin film material is disposed over a field enhancement element that includes sharp features to enhance concentration of an electric field in the film. In another example, measurement of structures with low sensitivity or mutually correlated parameters is enhanced by employing FEEs to generate electromagnetic resonances in the target element or between the target element and the FEE. In yet another example, measurement of overlay is enhanced by employing field enhancement elements.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 6 illustrates different plotlines associated with different pitch ratios.

DETAILED DESCRIPTION

Reference will now be made in detail to background examples and some embodiments of the invention, examples of which are illustrated in the accompanying drawings.

Systems and methods for measuring structural and material characteristics (e.g., material composition, dimensional characteristics of structures and films, etc.) associated with different semiconductor fabrication processes based on optical metrology are presented. In one aspect, a metrology system measures a specimen that includes field enhancement elements (FEEs), designed and constructed as part of the specimen, to enhance the measurement of structural elements of interest. In some embodiments, FEEs are constructed as part of a number of spatially periodic target elements to create or enhance metrology sensitivity to particular parameters of interest. In some embodiments, FEEs are constructed to enhance the measurement of the one or more thin film layers. In some examples, the FEEs are designed to enhance sensitivity to parameters to be measured. In some examples, the FEEs are designed to reduce correlations among parameters of interest and other parameters. By way of non-limiting example, FEEs may be employed to enhance the measurement of critical dimensions (CD), film thickness, film composition, and scatterometry overlay.

A wide variety of types of field enhancement elements may be constructed as part of the process flow for fabricating the device structures of interest. In some examples, the field enhancement provided by FEEs occurs in the areas where FEES are located. For example, a FEE may be a trench or a hole that increases field penetration to lower layers of a device stack. However, in other examples, the field enhancement provided by FEEs occurs in areas of away from the FEE location. For example, a FEE may be a beam steering element, prism element, or wave-guide element that directs the illumination field into an area of interest. In another example, a FEE may be a secondary grating element that couples the illumination field into an area of interest.

Figure 1:
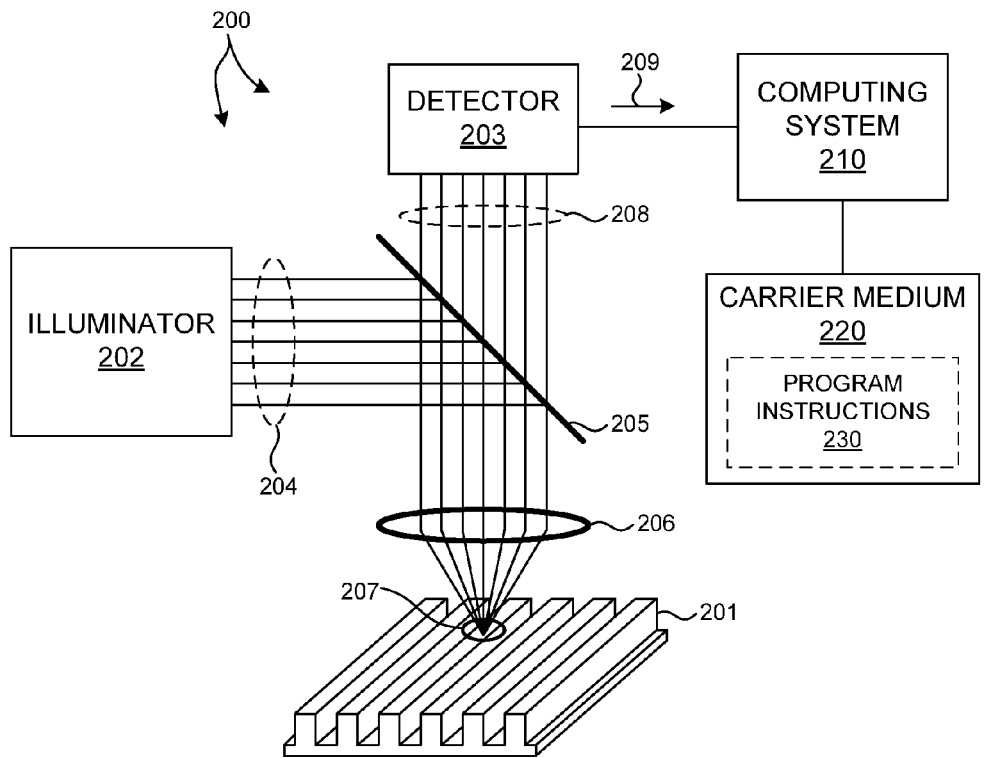
FIG. 1 illustrates a highly simplified schematic view of a metrology system 200 configured to detect light diffracted from a specimen that includes field enhancement elements and analyze the detected signals to determine parameters of interest in accordance with the methods presented herein.

FIG. 1 illustrates a highly simplified schematic view of a metrology system 200 configured to detect light diffracted from a specimen that includes field enhancement elements and analyze the detected signals to determine parameters of interest in accordance with the methods presented herein.

System 200 includes an illuminator 202 that delivers an illumination light 204. Illumination light 204 is directed toward a high-NA objective lens 206 by beam splitter 205. Objective lens 206 simultaneously illuminates specimen 201 over a target area 207 and collects diffracted light from specimen 201 over a wide range of angles. Field stops and apodizers (not shown) may be used to control spatial properties of illumination and collection beams. The collected light 208 is directed to detector 203 via beam splitter 205. In the depicted embodiment, detector 203 is a two dimensional array of charge coupled devices (CCD). Detector 203 detects collected light 208 and generates output signals 209 indicative of a pupil image of target area 207.

In some embodiments, illumination light 204 includes several wavelength channels. For example, illumination light 204 may be provided by multiple, different lasers. In some embodiments, system 200 includes different optical channels having different polarization and a waveplate to collect and measure relative phase difference between polarizations (not shown). In some embodiments, illuminator 202 is configured to provide multiple wavelengths simultaneously (e.g., a super-continuum laser source, a lamp source, or a laser-driven light source such as a laser sustained plasma).

In a further embodiment, the system 200 includes one or more computing systems 210 employed to analyze the output signals 209 to determine parameters of interest. The one or more computing systems 210 may be communicatively coupled to the detector 203. The one or more computing systems 210 are configured to receive the output signals 209 generated by detector 203.

It should be recognized that the various steps described throughout the present disclosure may be carried out by a single computer system 210, or alternatively, a multiple computer system 210. Moreover, different subsystems of the system 200, such as the detector 203, may include a computer system suitable for carrying out at least a portion of the steps described herein. Therefore, the description presented herein should not be interpreted as a limitation on the present invention but merely an illustration. Further, the one or more computing systems 210 may be configured to perform any other step(s) of any of the method examples described herein.

In another embodiment, the computer system 210 may be communicatively coupled to the detector 203 in any manner known in the art. For example, the one or more computing systems 210 may be coupled to a computing system of the detector 203. In another example, the detector 203 and the illuminator 202 may be controlled by a single computer system. In this manner, the computer system 210 may be coupled to the single computer system.

The computer system 210 may be configured to receive and/or acquire data or information from the subsystems of the system (e.g., detector 203, illuminator 202, and the like) by a transmission medium that may include wireline and/or wireless portions. In this manner, the transmission medium may serve as a data link between the computer system 210 and other subsystems of system 200. Further, the computing system 210 may be configured to receive images or residual signals via a storage medium (i.e., memory). For instance, the output signals 209 generated by detector 203 may be stored in a permanent or semi-permanent memory device (e.g., carrier medium 220). In this regard, the output signals may be imported from an external system. In another example, computer system 210 may send results generated by computer system 210 to a storage medium (e.g., carrier medium 220) to record the results.

Moreover, the computer system 210 may send data to external systems via a transmission medium. The transmission medium may include wireline and/or wireless portions. In this manner, the transmission medium may serve as a data link between the computer system 210 and other subsystems of system 200 or external systems. For example, computer system 210 may send results generated by computer system 210 to external systems or to other subsystems of system 200 via a transmission medium.

The computing system 210 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 230 implementing methods such as those described herein may be transmitted over or stored on carrier medium 220. The carrier medium may be a transmission medium such as a wire, cable, or wireless transmission link. The carrier medium may also include a computer-readable medium such as a read-only memory, a random access memory, a magnetic or optical disk, or a magnetic tape.

Figure 3:
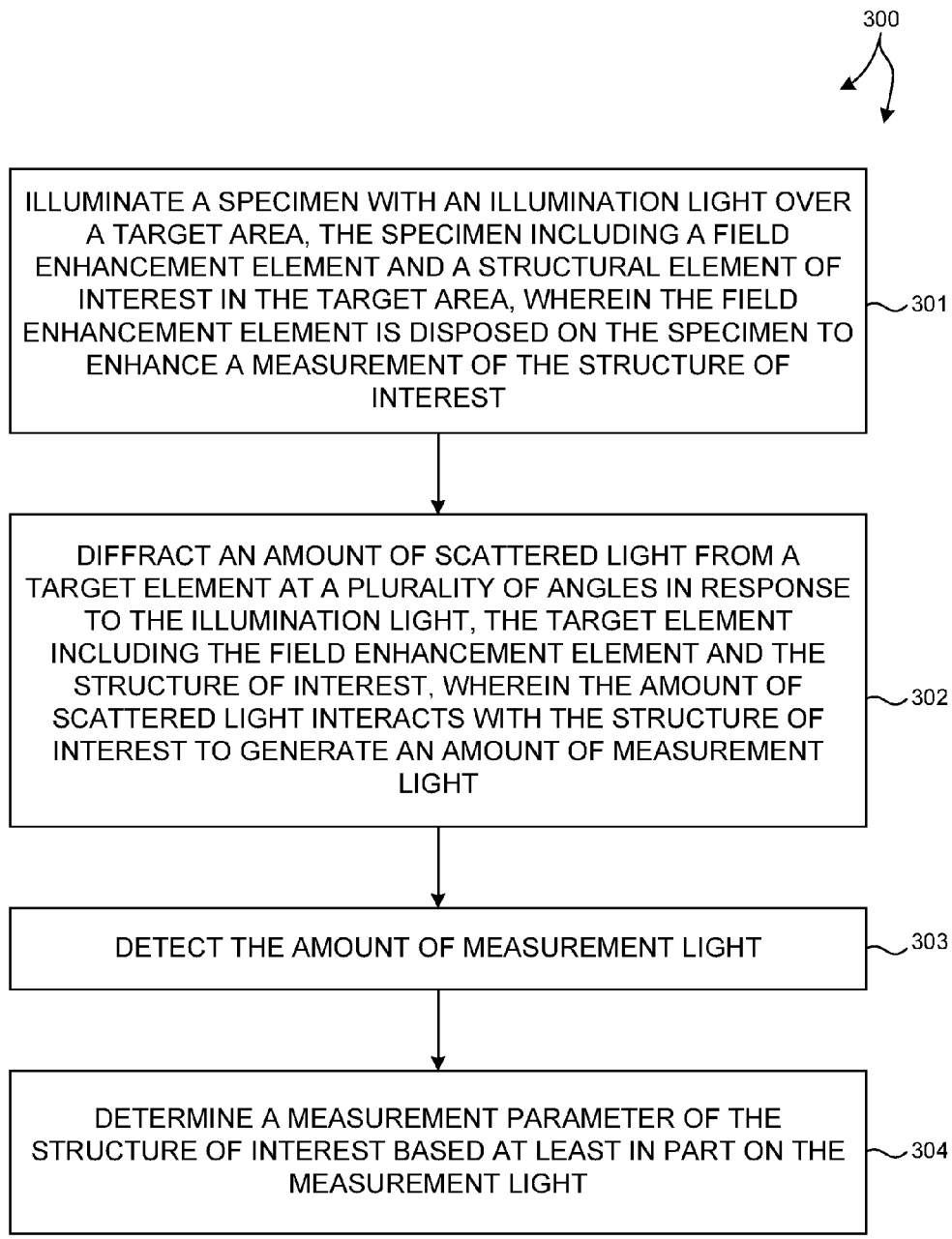
FIG. 3 illustrates a method 300 suitable for implementation by system 200 of the present invention.

FIG. 3 illustrates a method 300 suitable for implementation by system 200 of the present invention. In one aspect, it is recognized that data processing blocks of method 300 may be carried out via a pre-programmed algorithm stored as part of program instructions 230 and executed by one or more processors of computing system 210. While the following description is presented in the context of system 200 depicted in FIG. 1, it is recognized herein that the particular structural aspects of system 200 do not represent limitations and should be interpreted as illustrative only.

In block 301, system 200 illuminates a specimen 201 with an illumination light 204 over a target area 207 (i.e., area from which diffracted light is used for metrology or inspection). The specimen includes a field enhancement element and a structural element of interest in the target area. The field enhancement element is disposed on the specimen to enhance a measurement of the structure of interest. Often, specimen 201 includes an amount of die area to be used as part of the finished product and another amount of die area that will be sacrificed (e.g., by dicing processes, sawing processes, etc.) as part of the final production steps. In typical embodiments, field enhancement elements are disposed in the sacrificial area of the wafer. In this manner, field enhancement elements are used to enhance measurement of structures of interest without impacting the final product structure and performance.

In some embodiments, illuminator 202 is a laser light source. In some other embodiments, illuminator 202 is a high-brightness lamp source. The properties of illumination light 204 may be engineered, for example, by selecting light sources, single or multi-mode fibers, diffusers, scanning mirrors, and piezo stages, etc. In some embodiments, specimen 201 is illuminated at a number of different locations of specimen 201. In these embodiments, specimen 201 may be positioned under objective 206 by a wafer positioning system (not shown). For example, wafer positioning system may be a x-y translation stage or a rotary stage known in the art. Alternatively, or in conjunction with a wafer positioning system, illumination light 204 may be directed to different locations on specimen 201 by redirecting the illumination light 204. For example, a scanning mirror may be employed to redirect illumination light 204 to different locations on specimen 201.

In some examples, illumination light 204 is normally incident to specimen 201. In some other examples, illumination light 204 is incident to specimen 201 at an oblique angle. In some examples, illumination light is incident to specimen 201 over a range of angles of incidence. For example, in one embodiment, objective lens 206 has a high numerical aperture (e.g., NA of approximately 0.9). In this manner, illumination light 204 illuminates specimen 201 over a wide range of angles of incidence (e.g., a range of angles between zero and sixty four degrees for a system operating in air). Also, in some embodiments, in addition to illuminating specimen 201 over a range of angle of incidence, specimen 201 is illuminated by an illumination light 204 having a number of different polarization angles. Furthermore, in some embodiments, specimen 201 is illuminated by an illumination light 204 having a number of different wavelengths.

Figure 2:
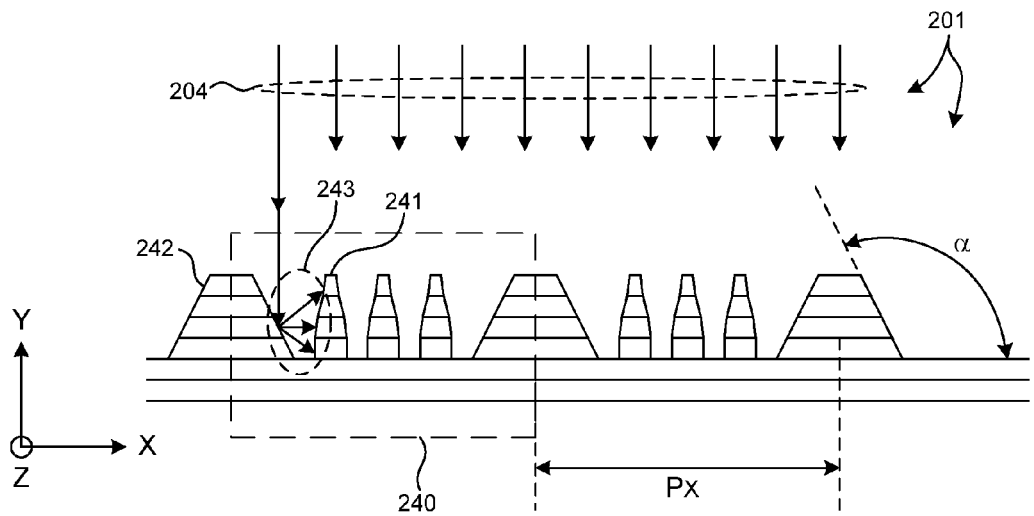
FIG. 2 is illustrative of a specimen 201 having a target element 240 that includes at least one field enhancement element 242 and at least one structure of interest 241.

As illustrated in FIG. 2, by way of example, illumination light 204 illuminates specimen 201. Specimen 201 includes a target element 240 that includes at least one field enhancement element 242 and at least one structure of interest 241. In some embodiments, target element 240 is a single, spatially repeating element (i.e., unit cell). In some embodiments, the target area 207 (i.e., area from which diffracted light is used for metrology or inspection) includes a number of spatially repeated target elements. Hence, a single measurement collects diffracted light from many target elements.

For example, as illustrated in FIG. 2, target element 240 is spatially repeated in the X-direction and each adjacent target element is separated from one another by a spatial period, Px. In another example (not shown), the target element 240 may also be spatially repeated in another direction not aligned with the X-direction (e.g., the Y-direction). For example, adjacent target elements are periodically repeated in the Y-direction and adjacent target elements are separated from one another by a spatial period, Py. Px and Py may be the same or different. In this manner, metrology systems have the ability to perform measurements over a target area that includes a number of spatially repeated target elements that generate a grating effect in the output signals that may simplify the subsequent determination of parameters of interest.

In block 302, a portion of illumination light 204 diffracts from the target element 240 at a plurality of angles to generate an amount of scattered illumination light 243. The scattered illumination light 243 interacts with the structure of interest to generate an amount of measurement light (not shown) that is subsequently collected by system 200. By diffracting a portion of the illumination light 204 from field enhancement elements 242 over a range of angles (as illustrated in FIG. 2), a structure of interest 243 is illuminated from a wide range of angles that would not be accessible by direct illumination from system 200 without the presence of the field enhancement element. As a result, measurement light generated by interaction between the scattered illumination light 243 and a structure of interest 241 includes information that would not be present without illumination by the scattered illumination light 243 over a range of angles.

Although, the field enhancement mechanism is illustrated in FIG. 2 as a collection of light rays, actual measurement involves diffraction of the complete electromagnetic field. The light diffracted from the field enhancement element 242 includes the zero diffraction order (i.e. specularly reflected light), but may also include higher diffraction orders. If measurement results are to be derived primarily from zero diffraction order light, the spatial period between adjacent target elements 240 should be on the order of the wavelength of the illumination light or smaller. However, the use of light having higher diffraction orders allows the spatial period between target elements to be larger than the wavelength of the illumination light.

As illustrated in FIG. 2, by way of example, a field enhancement element 242 is shaped such that it includes a sidewall that is oriented at an oblique angle, $\alpha$, with respect to the surface of specimen 201. More specifically, as depicted in FIG. 2, field enhancement element 242 is shaped as a trapezoid having a height, sidewall angle, and width. In addition, adjacent field enhancement elements are separated by a spatial period, Px. In this manner, light diffracted from the surface of field enhancement element 242 is directed toward a structure of interest 241 over a range of angles. The shape and location of the field enhancement element (e.g., side wall angle (SWA), distance to structure of interest, number of field enhancement elements in a target element 240, spatial pitch of target elements 240 are all exemplary parameters designed to enhance measurement results. The illustration of FIG. 2 is presented by way of non-limiting example as many other shapes of field enhancement elements may be contemplated. Additional, non-limiting examples are presented herein.

In block 303, an amount of measurement light is detected by system 200. As illustrated in FIG. 1, detector 203 generates a plurality of output signals 209, indicative of an amount of measurement light collected from the specimen 201. In some embodiments, detector 203 includes a two dimensional array of CCD elements. In some other embodiments, detector 203 includes a one dimensional array of CCD elements. Other detector elements may be contemplated (e.g., photodetectors, etc.). Hence, in general, system 200 may be one dimensional (e.g., employing a one dimensional array of photodiodes) or two dimensional (e.g., employing a two dimensional CCD array). In some embodiments, the plurality of output signals is assembled to generate an image of specimen 201. In addition, in many examples, a number of measurements may be performed for different polarization and wavelength channels to generate a number of output signals that enhance measurement performance.

In block 304, computer system 210 determines a measurement parameter of a structure of interest based at least in part on the detected measurement light. The nominal scatterometry measurement process consists of parameterization of the structure (e.g., film thicknesses, critical dimensions, dispersion curves, etc.) and the system (e.g., wavelengths, angles of incidence, polarization angles, etc.). Certain parameters are treated as known, fixed parameters and other parameters are treated as unknown, floating parameters. The floating parameters are resolved by a process (e.g., regression) that produces the best fit between theoretical predictions and experimental data.

In another example, computer system 210 determines an image of the target element by determining a difference between output signals associated with a particular image and a model of the expected nominal structure. As discussed hereinbefore, nominal parameter values may be resolved by a process (e.g., regression) that produces the best fit between theoretical predictions and experimental data over a number of wavelengths, polarization states, etc. In this manner, parameters are determined based on differences between measured images and a best fit model of the expected nominal structure.

In some embodiments, measurement of high-aspect ratio structures of interest is enhanced by employing field enhancement elements to steer or concentrate illumination light into dark recesses of the target element. In this manner penetration of illumination light into the target element is enhanced along with access to vertical layer information.

Figure 4:
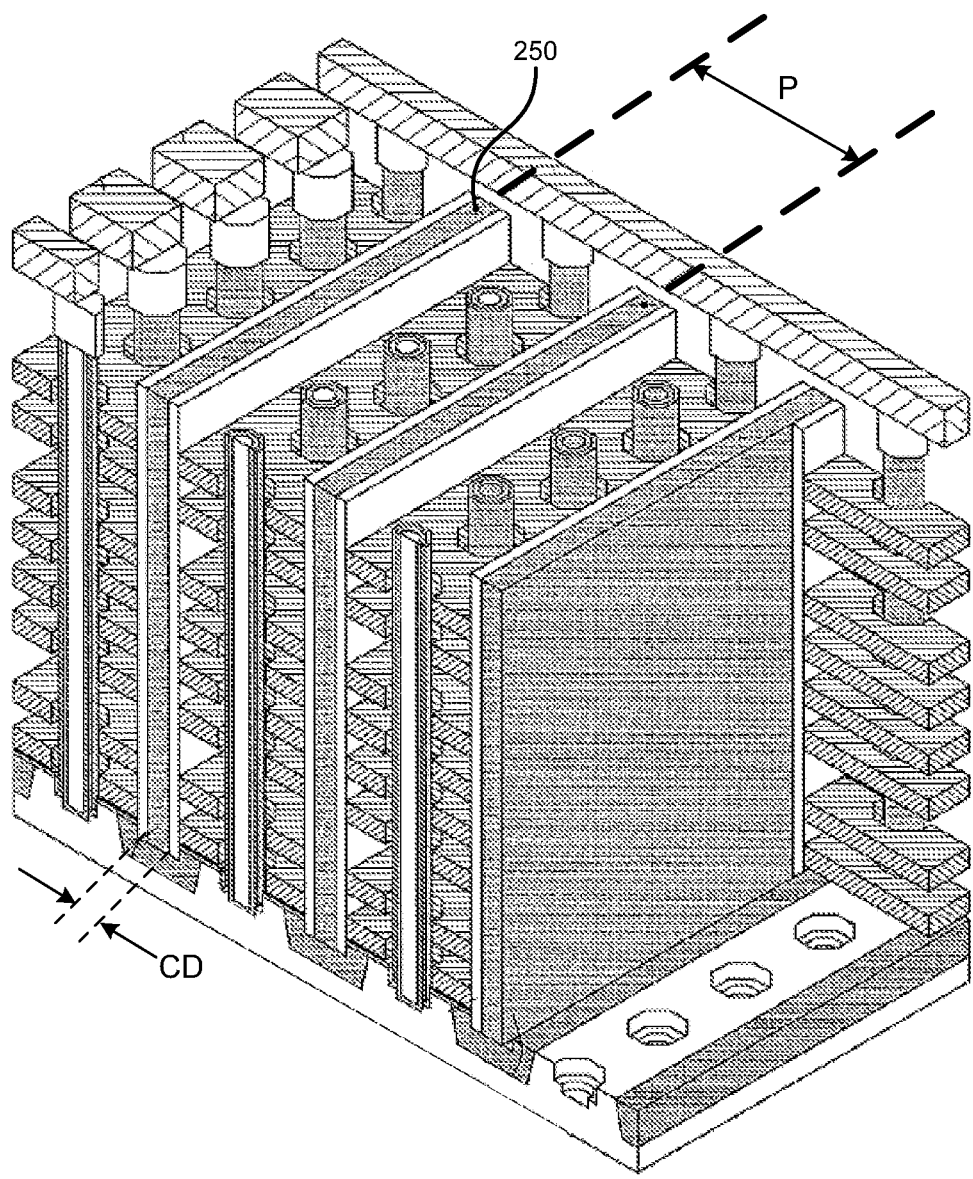
FIG. 4 is illustrative of a measurement of vertical flash layers of a flash memory structure enhanced by a field enhancement element.

FIG. 4 is illustrative of a measurement of vertical flash layers of a flash memory structure enhanced by a field enhancement element. Further information about the memory structure may be found in U.S. Pat. Pub. No. 2011/0233648 A1 published on Sep. 29, 2011, and assigned to Samsung Electronics Co., LTD., the entirety of which is incorporated herein by reference. As illustrated in FIG. 4, field enhancement elements 250 are added as trenches on either side of the bit line via array. A key factor limiting measurement performance in these devices is the reduction in light intensity as the spectroscopic ellipsometer or reflectometer illumination light propagates towards the silicon substrate from the device surface. This results in a reduced measurement sensitivity to the bottom critical dimension (BCD) of the via hole which subsequently forms the flash cell bit line. In addition, measurement sensitivity to individual layers near the bottom of the film stack is also reduced. A field enhancement element 250 is added to increase the optical field penetration at the bottom of the device.

A trench etch is typically performed in preparation for creating a word line structure in the flash cell. The flash cell layout is designed to accommodate this word line trench. However, the position and/or spacing of the trench in typical flash cell layouts may not be optimum for improving BCD and bottom thickness sensitivity. In this example, the design of the field enhancement element (i.e., trench) is optimized to enhance BCD and bottom thickness sensitivity by proper selection of the FEE pitch and CD.

Figure 5:
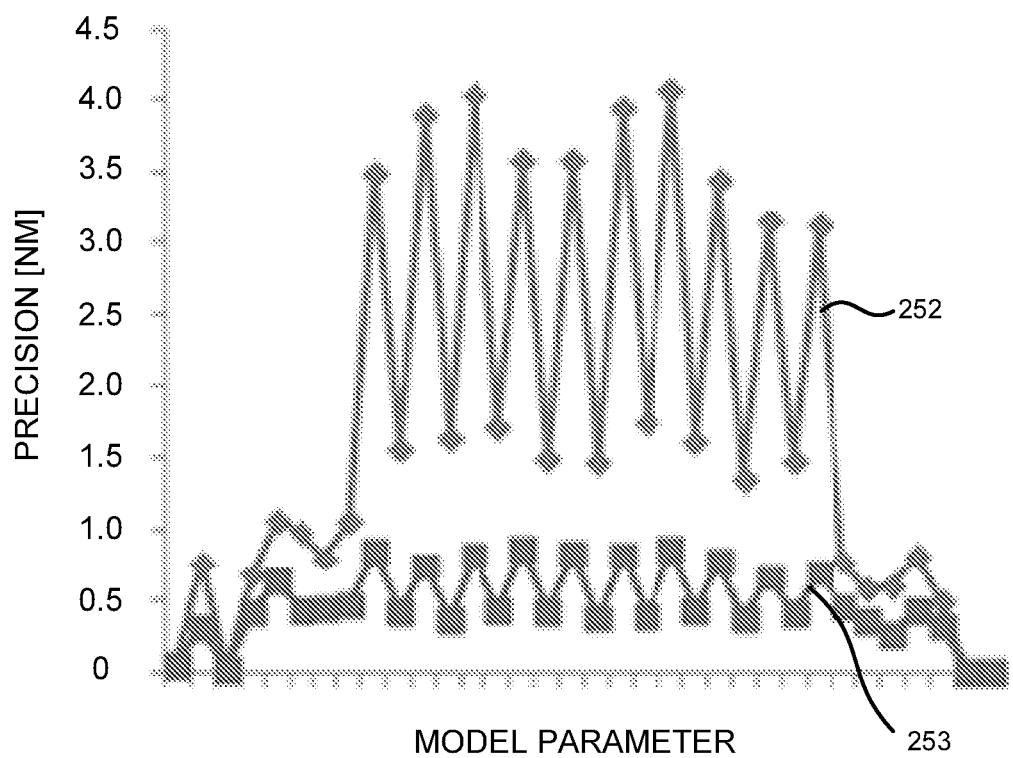
FIG. 5 is a plot illustrative of an improvement in measurement precision for various model parameters using specifically designed field enhancement elements (i.e., trenches).
Figure 6:
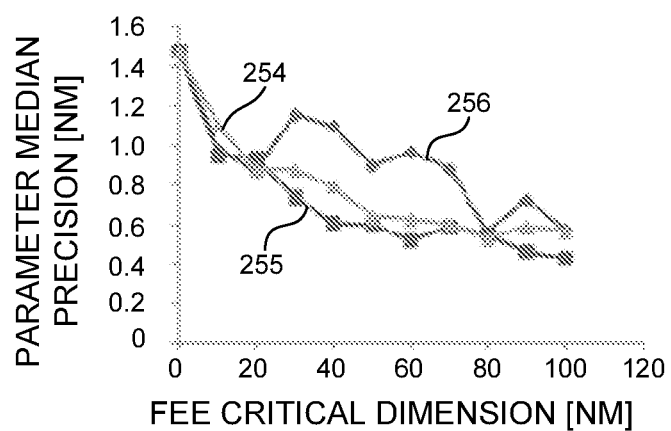
FIG. 6 is a plot illustrative of an improvement in measurement precision with an increasing critical dimension (CD) of each field enhancement element 250. In addition.

FIG. 5 is a plot illustrative of an improvement in measurement precision for various model parameters using specifically designed field enhancement elements (i.e., trenches). In this embodiment the size of each trench is selected to be one hundred nanometers wide with spacing between trenches of two hundred nanometers to improve measurement performance. In this example, the measurement precision of model parameters including critical dimensions and layer thicknesses through the depth of the stack are plotted. Plotline 252 illustrates the case where no changes to the nominal structure are made. Plotline 253 illustrates the case where the field enhancement elements are designed to enhance measurement performance. As illustrated in FIG. 6, the measurement precision improves with an increasing critical dimension (CD) of each field enhancement element 250. In addition, FIG. 6 illustrates different plotlines associated with different pitch ratios (i.e., ratio of FEE spacing to FEE CD). Plotlines 256, 255, and 254 correspond to pitch ratios 1:1, 2:1, and 3:1, respectively. As illustrated in FIG. 6, it appears that a pitch ratio of 2:1 (illustrated by plotline 255) delivers the best measurement result. In addition to improved measurement sensitivity, parameter correlation is also reduced.

In some embodiments, measurement of thin film layers is enhanced by employing field enhancement elements such that measurement data can be analyzed to isolate parameters associated with particular layers. For example, film thickness measurements are often complicated by the presence of opaque layers (e.g., metal layers). Similarly, composition measurements are often complicated by low sensitivity to certain measured parameters (e.g., nitrogen percentage). FEEs are introduced into the target area to enhance measurement results by enabling the isolation of the parameters of interest.

Figure 7A:
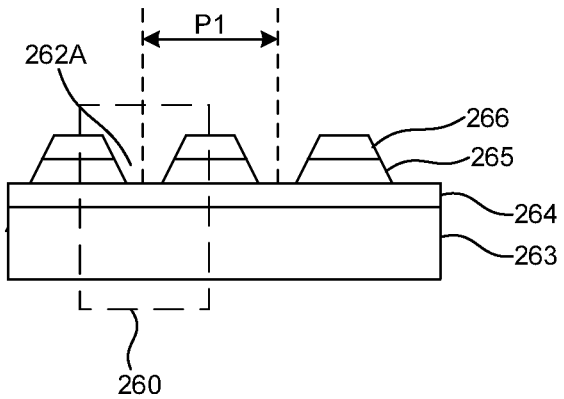
FIGS. 7A and 7B are illustrative of a multi-layer specimen 201 that includes a substrate 263, a first layer 264, a second layer 265, and a third layer 266.
Figure 7B:
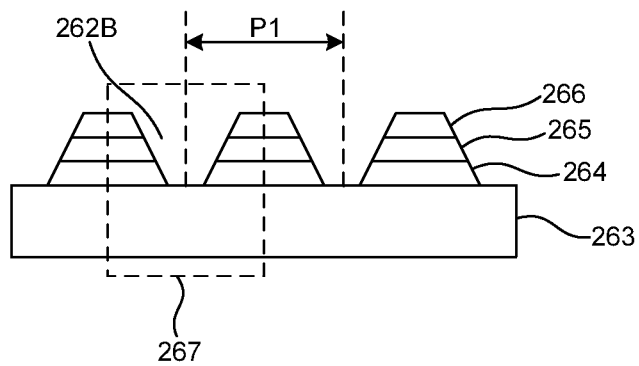

In some embodiments, measurements of multiple target elements are combined in a multi-target analysis to isolate particular parameters of interest. FIGS. 7A and 7B are illustrative of a multi-layer specimen 201 that includes a substrate 263, a first layer 264, a second layer 265, and a third layer 266. As illustrated in FIG. 7A, target element 260 includes a field enhancement element 262A. Adjacent target elements are separated from one another by a spatial period P1. In the illustrated example, field enhancement element 262A is a trench. As illustrated in FIG. 7B, target element 267 includes a field enhancement element 262B. Adjacent target elements are separated from one another by a pitch P1. In the illustrated example, field enhancement element 262B is also a trench. However, FEE 262B is shaped differently than FEE 262A. More specifically, FEE 262B is etched deeper than FEE 262A. In one example, layer 264 is a structure of interest. As depicted in FIG. 7A, layers 265 and 266 are etched through to layer 264 within target element 260. As depicted in FIG. 7B, layer 264 is also etched through, in addition to layers 265 and 266 within target element 267. In this multi-target example (i.e., target elements 260 and 267), the structure of interest (layer 264) is isolated using two different target elements. The common layers (i.e., layers 265 and 266) are linked in a multi-target analysis and the structure of interest (e.g., thickness, composition, or profile) is floated and solved by, for example, regression analysis. In other examples, multi-target analysis may be expanded to isolate and measure different layers or combinations of layers.

Figure 8:
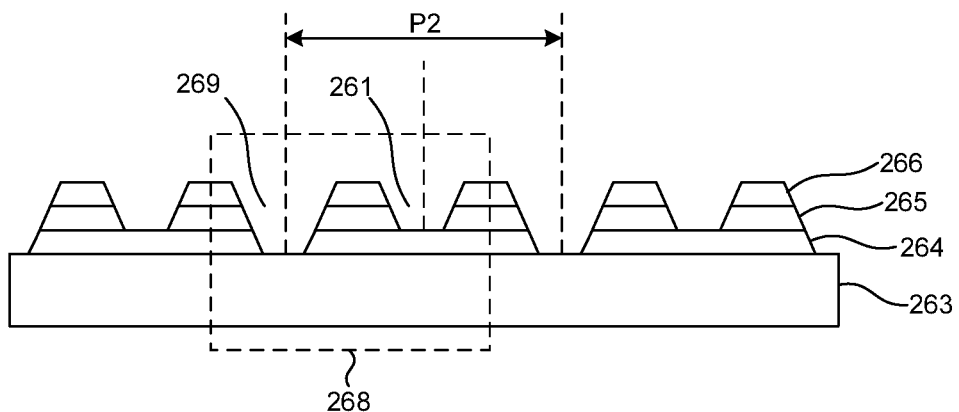
FIG. 8 is illustrative of a multi-layer specimen that includes an individual target element having two different field enhancement elements.

In some embodiments, measurements of different parameters of interest are enhanced by a single target element that includes more than one differently shaped FEE. FIG. 8 is illustrative of a multi-layer specimen similar to that described with reference to FIGS. 7A-7B. However, as illustrated in FIG. 8, an individual target element 268 includes two differently shaped field enhancement elements, field enhancement element 261 and field enhancement element 269. The field enhancement element 261 is etched to layer 264 and field enhancement element 269 is etched through layer 264. In this single-target example (i.e., target element 268), one structure of interest (layer 265) is isolated using a first FEE (FEE 261) and a second structure of interest (layer 264) is isolated using a second, differently shaped FEE (FEE 269). In this embodiment, two different field enhancement elements are etched to different levels. In a single-target analysis the structures of interest (e.g., thickness, composition, or profile) are floated and solved by, for example, regression analysis. Similarly, different target elements may be constructed to isolate and measure different layers. In addition, spatially repeating target elements may be employed to enhance measurement performance. As illustrated in FIG. 8, target element 268 is spatially repeated and adjacent target elements are separated from one another by a spatial period, P2.

Figure 9A:
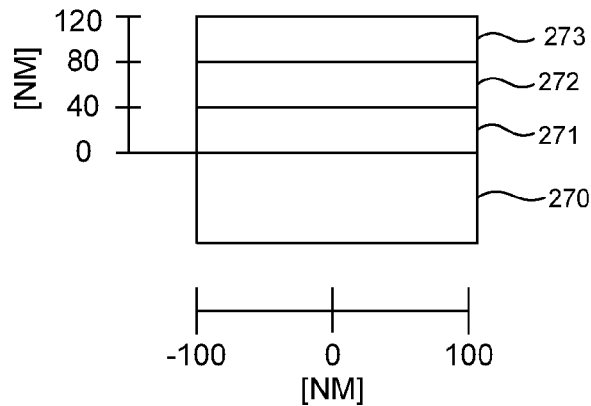
FIGS. 9A-9C are illustrative of another multi-layer specimen that includes a silicon substrate 270, a polysilicon layer 271, a titanium layer 272, and a titanium nitride layer 273.
Figure 9B:
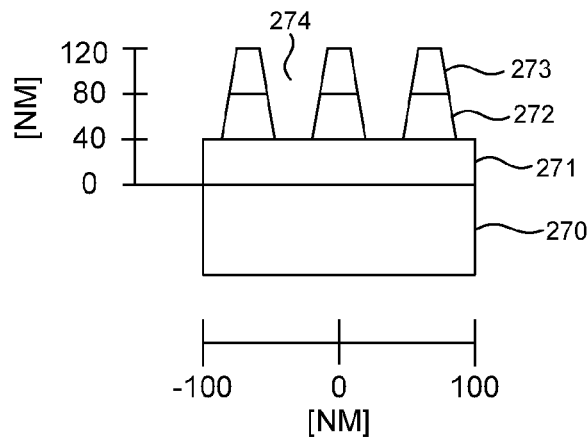
Figure 9C:
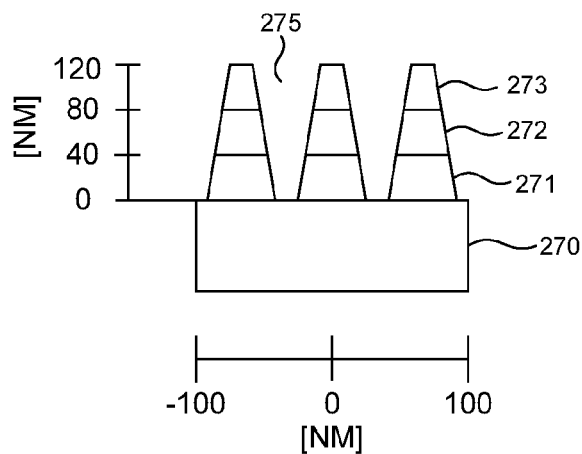

FIGS. 9A-9C are illustrative of another multi-layer specimen that includes a silicon substrate 270, a polysilicon layer 271, a titanium layer 272, and a titanium nitride layer 273. Each layer is approximately forty nanometers thick. Field enhancement elements are fabricating as trenches in the specimen to enhance the measurement of thickness of polysilicon film layer 271. As illustrated in FIG. 9A, a measurement of polysilicon layer 271 is difficult because of the presence of the metal layers above. As illustrated in FIG. 9B, the FEE 274 extends to layer 271. As illustrated in FIG. 9C, FEE 275 extends through layer 271.

Figure 10:
FIG. 10 depicts a chart 10 illustrative of an improvement in measurement performance achieved by measuring a target specimen that includes FEEs.

FIG. 10 depicts a chart 10 that illustrates the improvement in measurement performance achieved by employing FEEs as part of the target specimen. A spectroscopic ellipsometry measurement of the layer 271 thickness without a field enhancement element shows very low sensitivity and poor precision. However, by performing a single target analysis on a target element such as illustrated in FIG. 9C, sensitivity is greatly increased and precision is greatly improved. Further, improvement in measurement performance is obtained by performing a multi-target analysis using a target element such as illustrated in FIG. 9B and a target element such as illustrated in FIG. 9C.

Figure 11:
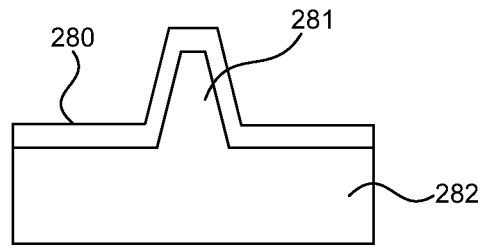
FIG. 11 is a diagram illustrative of a silicon oxide film coating 280 over a silicon field enhancement element 281.

In some embodiments, a thin film material is disposed over a field enhancement element that is shaped (e.g., includes sharp features) to enhance concentration of an electric field in the film. FIG. 11 is a diagram illustrative of a silicon oxide film coating 280 over a silicon field enhancement element 281. Field enhancement element 281 introduces a sharp feature (e.g., corners of trapezoid shaped FEE 281) into the structure of interest (film 280) that concentrates illumination light area(s) of interest. Sharp features with high refractive index contrast attract stronger electric fields. By increasing the electric field in the area(s) of interest, sensitivity to film parameters (e.g., critical dimensions, film thicknesses, and composition parameters) is increased. More specifically, the sharp feature of FEE 281 on a flat surface of silicon substrate 282 enhances the electric field around the top of FEE 281. In this manner, the field is concentrated in the area of the film on the top of the FEE 281. The shape and dimensions of the FEE 281 may be optimized to improve sensitivity at a particular polarization angle, wavelength, etc.

Figure 12:
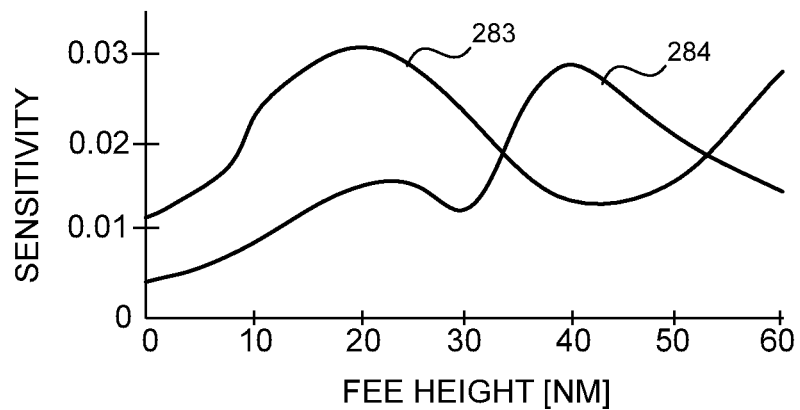
FIG. 12 depicts a plot illustrative of the impact of FEE height on measurement sensitivity.

FIG. 12 depicts a plot illustrative of the impact of the height of FEE 281 on measurement sensitivity based on finite element model calculations. The presence of FEE 281 improves measurement sensitivity to film thickness over the full range of heights plotted. Plotline 283 shows the results for P-polarized illumination light. The measurement sensitivity for P-polarized light is maximized at a FEE height of approximately twenty nanometers. Plotline 284 shows the results for S-polarized illumination light. The measurement sensitivity for S-polarized light is maximized at a FEE height of approximately forty nanometers. In this manner, FEE height may be designed to maximize measurement sensitivity for a particular polarization angle. In addition, FEEs for different films may vary in shape and size to increase sensitivity only at certain angles of incidence and wavelength.

Figure 13:
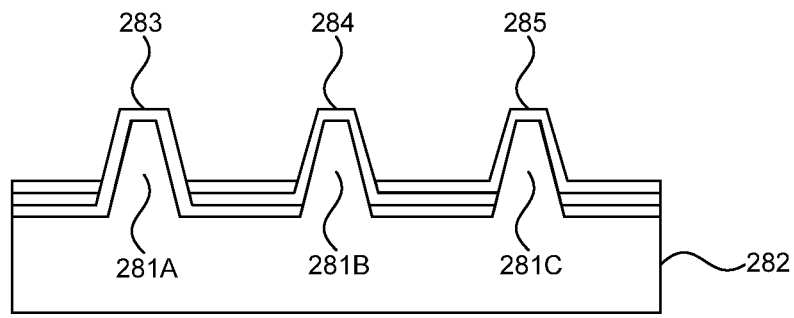
FIG. 13 is illustrative of a number of field enhancement elements 281A-C, each coated with a different film layer.

FIG. 13 is illustrative of a number of field enhancement elements 281A-C, each coated with a different film layer. Each field enhancement element is used to concentrate electric field on a particular film in the film stack. As illustrated, measurement of film 283 is enhanced by field enhancement element 281A, measurement of film 284 is enhanced by field enhancement element 281B, and measurement of film 285 is enhanced by field enhancement element 281C.

In another example, measurement of structures with low sensitivity or mutually correlated parameters is enhanced by employing FEEs to generate electromagnetic resonances in the target element or between the target element and the FEE.

Figure 14A:
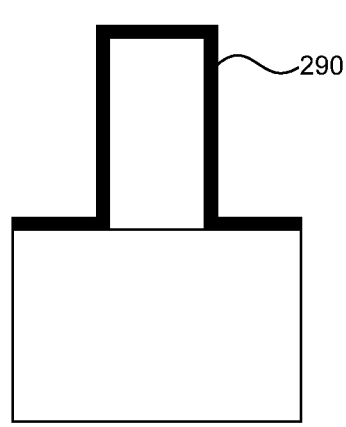
FIGS. 14A-14B are illustrative of thin film dielectric structures enhanced by field enhancement elements to create resonances which are highly sensitive to nitrogen concentration.
Figure 14B:
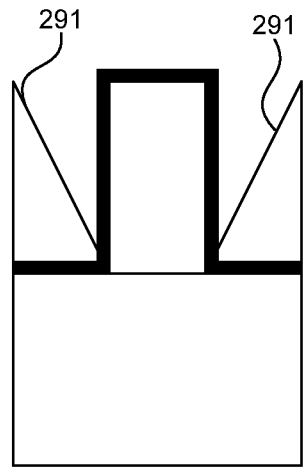

In many examples, thin films, such as thin film 290 illustrated in FIG. 14A, are used to create dielectric gates during the fabrication of semiconductor devices. Advanced three dimensional transistor structures, such as FinFETs, are being fabricated as part of the ongoing effort to shrink device sizes. Nitrogen is added to the gate dielectric material to achieve the desired characteristics of these structures. The amount of nitrogen added must be accurately controlled, hence a precise measurement of nitrogen concentration is required. To increase the sensitivity to nitrogen concentration in advanced three dimensional structures, periodic field enhancement elements, such as FEE 291 as illustrated in FIG. 14B, are added in plane to the target to create resonances which are highly sensitive to nitrogen concentration. Spectroscopic scatterometry modeling shows that the addition of specially designed field enhancement elements increases the sensitivity of the Fourier coefficients $\alpha$ and $\beta$ to nitrogen concentration in three dimensional FinFET structures because of a strong field enhancement at 200 nm around the bottom edges of the FinFET.

Figure 15:
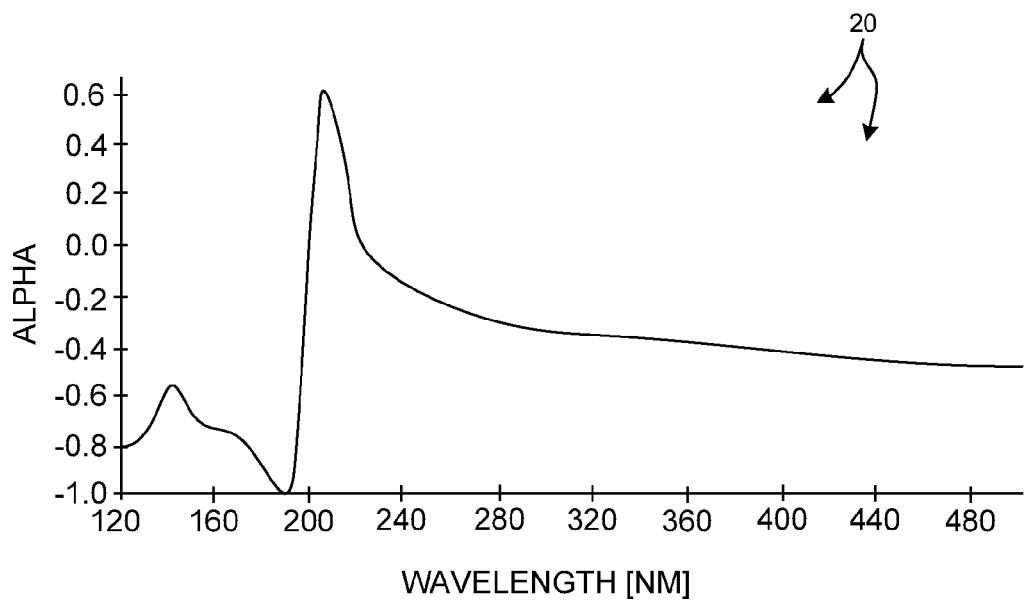
FIG. 15 is illustrative of a plot 20 of a as a function of illumination wavelength.
Figure 16:
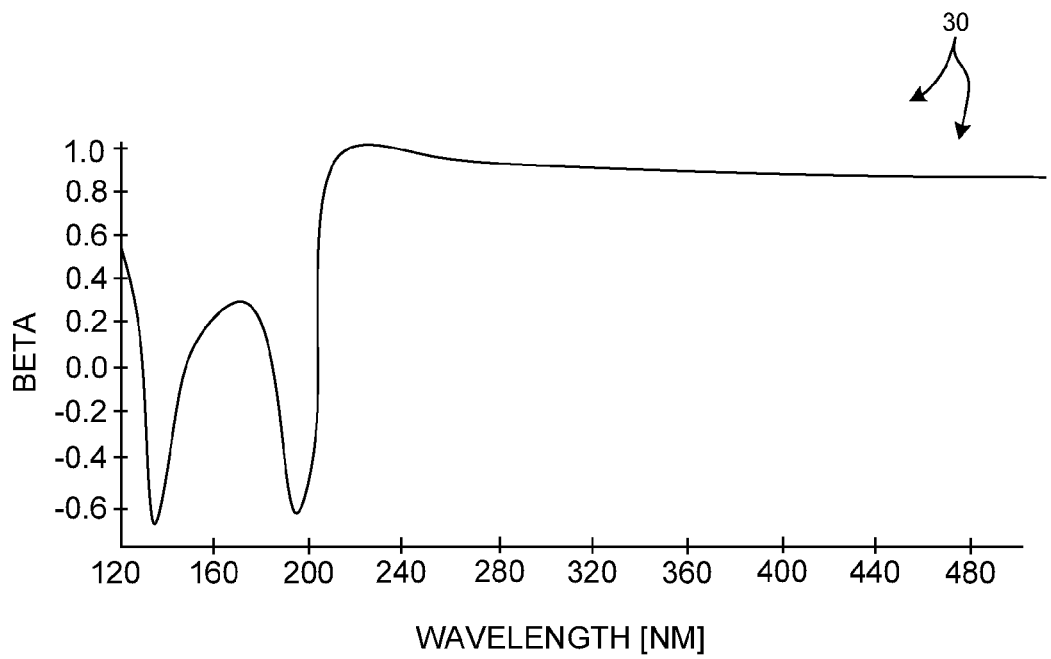
FIG. 16 illustrates a plot 30 of p as a function of illumination wavelength.

FIG. 15 illustrates a plot 20 of $\alpha$ as a function of illumination wavelength. For illumination light with a wavelength of 200 nm, the sensitivity of $\alpha$ with respect to nitrogen concentration increases by a factor of 60 with the addition of field enhancement elements. Similarly, FIG. 16 illustrates a plot 30 of $\beta$ as a function of illumination wavelength. For illumination light with a wavelength of 200 nm, the sensitivity of $\beta$ with respect to nitrogen concentration increases by a factor of 400 with the addition of field enhancement elements.

Figure 17:
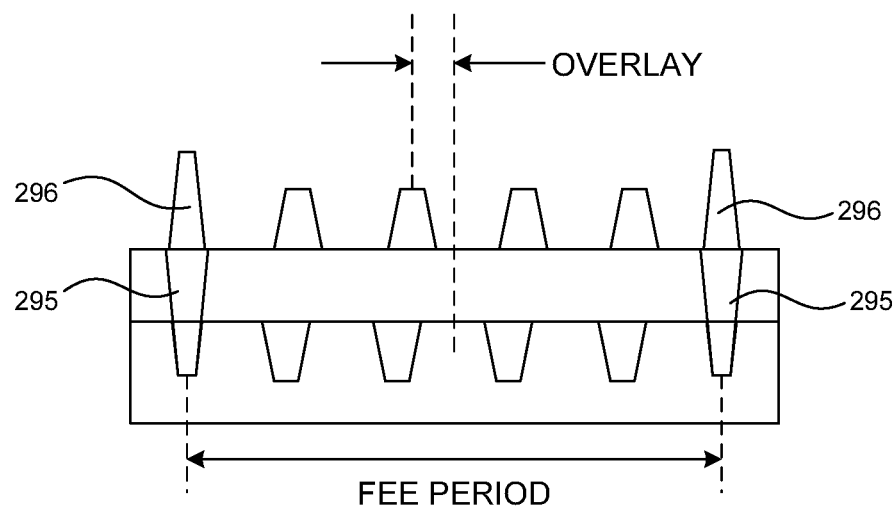
FIG. 17 illustrates two possible FEE configurations, additive and subtractive FEEs, to enhance measurement of overlay.

In yet another example, measurement of overlay is enhanced by employing field enhancement elements. Scatterometry Overlay (SCOL) is a technique in which the difference in spectral reflectance or ellipsometric signal between two targets having an overlay difference is used to determine the amount of the overlay. In some examples, field enhancement elements are added to such targets to enhance the sensitivity of the difference signal to overlay changes. FIG. 17 illustrates two possible FEE configurations. In one embodiment, material is removed from the specimen to create a subtractive FEE (e.g. trenches). By way of example, FEEs 295 are subtractive FEEs. In another embodiment, material is added to the specimen to create an additive FEE. By way of example, FEEs 296 are additive FEEs. The FEEs (e.g., any of FEEs 295 and 296) are added to the SCOL targets using a single, separate mask operation, so that overlay shifts between the FEE and the underlying targets would be the same for both targets. The FEE dimensions and pitch could be designed and optimized to alter the local optical field and diffraction conditions in such a way that overlay sensitivity for the targets is enhanced. In some examples, metal structures would be used as FEE materials.

In some examples, FEEs directly enhance measurement sensitivity or reduce parameter correlations associated with measurement of a particular target element. In these single target examples the data collected from a single target element (or repeated single target elements) is used determine measurement parameters. In some other examples, FEEs enhance the measurement sensitivity or reduce parameter correlations associated with measurement of a number of different target elements (i.e., target elements that include differently shaped FEEs) as a part of multi-target optimization. A multi-target measurement involves data collection from different target elements to determine measurement parameters. For example, a number of multi-target analysis techniques are described in U.S. Pat. No. 7,478,019, assigned to KLA-Tencor, Corp., which is incorporated herein by reference in its entirety. Multi-target measurements may involve a number of different target elements employing different FEEs. In addition, multi-target measurements may involve measurements of target elements that do not include a FEE. In these multi-target examples, a set of FEEs are designed to both enhance the measurement of each target element and the entire set of multiple targets.

Although the methods discussed herein are explained with reference to system 200, any optical metrology system configured to illuminate and detect light diffracted from a specimen may be employed to implement the exemplary methods described herein. Examplary systems include an angle-resolved reflectometer (or scatterometer), a reflectometer or ellipsometer. A system implementing the methods described herein may also be configured in a number of different ways. For example, a wide range of wavelengths (including visible, ultraviolet, infrared, and X-ray), angles of incidence, states of polarization, and states of coherence may be contemplated.

Figure 18:
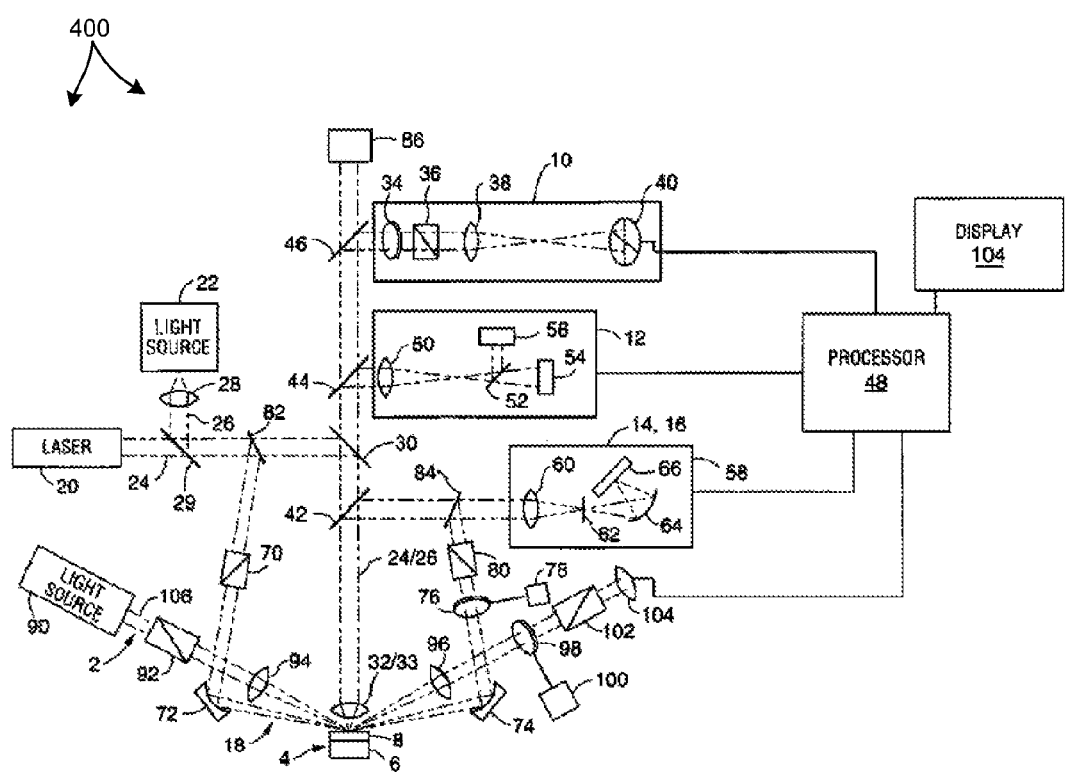
FIG. 18 illustrates a path-based parallel discrete polarization scatterometer 400 in one exemplary embodiment that is suitable to implement the methods described herein.

A preferred embodiment of a suitable system 400 is illustrated in FIG. 18, and is more fully described in U.S. Pat. No. 7,567,351 assigned to KLA-Tencor Corp., which is incorporated herein by reference in its entirety. FIG. 18 illustrates a path-based parallel discrete polarization scatterometer 400 in one exemplary embodiment.

The apparatus of FIG. 18 includes five different non-contact optical measurement devices as well as a narrow band, off-axis ellipsometer 2 for measuring a sample 4 including a substrate 6 and a region 8 of repeating structures as would be present in a typical memory die. The composite optical measurement system includes a Beam Profile Ellipsometer (BPE) 10, a Beam Profile Reflectometer (BPR) 12, a Broadband Reflective Spectrometer (BRS) 14, a Deep Ultra Violet Reflective Spectrometer (DUV) 16, and a Broadband Spectroscopic Ellipsometer (BSE) 18. These five optical measurement devices utilize as few as two optical sources: laser 20 and light source 22. Laser 20 generates a probe beam 24, and light source 22 generates probe beam 26 (which is collimated by lens 28 and directed along the same path as probe beam 24 by mirror 29). Laser 20 ideally is a solid-state laser diode which emits a linearly polarized beam. Light source 22 is ideally a combination of two lamps, deuterium and tungsten or Xenon bulb, that produces a polychromatic beam that covers a spectrum of 190 nm to 820 nm. The probe beams 24/26 are reflected by mirror 30, and pass through mirror 42 to sample 4.

The probe beams 24/26 are focused onto the surface of the sample with a lens 32 or lens 33. In the preferred embodiment, two lenses 32/33 are mounted in a turret (not shown) and are alternatively movable into the path of probe beams 24/26. Lens 32 is a spherical, microscope objective lens with a high numerical aperture (on the order of 0.90 NA) to create a large spread of angles of incidence with respect to the sample surface, and to create a spot size of about one micron in diameter. Lens 33 is a reflective lens having a lower numerical aperture (on the order of 0.4 NA) and capable of focusing deep UV light to a spot size of about 10 to 15 microns.

Beam profile ellipsometry (BPE) is discussed in U.S. Pat. No. 5,181,080, issued Jan. 19, 1993, which is commonly owned by the present assignee and is incorporated herein by reference. BPE 10 includes a quarter wave plate 34, polarizer 36, lens 38 and a detector 40. In operation, linearly polarized probe beam 24 is focused onto sample 4 by lens 32. Light reflected from the sample surface passes up through lens 32, through mirrors 42, 30 and 44, and directed into BPE 10 by mirror 46. The position of the rays within the reflected probe beam correspond to specific angles of incidence with respect to the sample's surface. Quarter-wave plate 34 retards the phase of one of the polarization states of the beam by 90 degrees. Linear polarizer 36 causes the two polarization states of the beam to interfere with each other. For maximum signal, the axis of the polarizer 36 should be oriented at an angle of 45 degrees with respect to the fast and slow axis of the quarter-wave plate 34. Detector 40 is a quad-cell detector with four radially disposed quadrants that each intercept one quarter of the probe beam and generate a separate output signal proportional to the power of the portion of the probe beam striking that quadrant. The output signals from each quadrant are sent to a processor 48. As discussed in the U.S. Pat. No. 5,181,080 patent, by monitoring the change in the polarization state of the beam, ellipsometric information, such as .psi. and .DELTA., can be determined. To determine this information, the processor 48 takes the difference between the sums of the output signals of diametrically opposed quadrants, a value which varies linearly with film thickness for very thin films. This analysis is sometimes referred to herein as the "diff" signal. Adding the output from the four quadrants is referred to as the "sum" signal which can also provide useful information.

Beam profile reflectometry (BPR) is discussed in U.S. Pat. No. 4,999,014, issued on Mar. 12, 1991, which is commonly owned by the present assignee and is incorporated herein by reference. BPR 12 includes a lens 50, beam splitter 52 and two linear detector arrays 54 and 56 to measure the reflectance of the sample. In operation, linearly polarized probe beam 24 is focused onto sample 4 by lens 32, with various rays within the beam striking the sample surface at a range of angles of incidence. Light reflected from the sample surface passes up through lens 32, through mirrors 42 and 30, and directed into BPR 12 by mirror 44. The position of the rays within the reflected probe beam correspond to specific angles of incidence with respect to the sample's surface. Lens 50 spatially spreads the beam two-dimensionally. Beam splitter 52 separates the S and P components of the beam, and detector arrays 54 and 56 are oriented orthogonal to each other to isolate information about S and P polarized light. The higher angles of incidence rays will fall closer to the opposed ends of the arrays. The output from each element in the diode arrays will correspond to different angles of incidence. Detector arrays 54/56 measure the intensity across the reflected probe beam as a function of the angle of incidence with respect to the sample surface. The processor 48 receives the output of the detector arrays 54/56.

Broadband reflective spectrometer (BRS) 14 simultaneously probes the sample 4 at normal incidence with multiple wavelengths of light. BRS 14 uses lens 32 and includes a broadband spectrometer 58 which can be of any type commonly known and used in the prior art. The spectrometer 58 shown in FIG. 1 includes a lens 60, aperture 62, dispersive element 64 and detector array 66. During operation, probe beam 26 from light source 22 is focused onto sample 4 by lens 32. Light reflected from the surface of the sample passes up through lens 32, and is directed by mirror 42 (through mirror 84) to spectrometer 58. The lens 60 focuses the probe beam through aperture 62, which defines a spot in the field of view on the sample surface to analyze. Dispersive element 64, such as a diffraction grating, prism or holographic plate, angularly disperses the beam as a function of wavelength to individual detector elements contained in the detector array 66. The different detector elements measure the optical intensities (magnitude) of the different wavelengths of light contained in the probe beam, preferably simultaneously. Alternately, detector 66 can be a CCD camera, or a photomultiplier with suitably dispersive or otherwise wavelength selective optics. It should be noted that a monochrometer could be used to measure the different wavelengths serially (one wavelength at a time) using a single detector element. Further, dispersive element 64 can also be configured to disperse the light as a function of wavelength in one direction, and as a function of the angle of incidence with respect to the sample surface in an orthogonal direction, so that simultaneous measurements as a function of both wavelength and angle of incidence are possible. Processor 48 processes the intensity information measured by the detector array 66.

Deep ultra violet reflective spectrometry (DUV) simultaneously probes the sample with multiple wavelengths of ultra-violet light. DUV 16 uses the same spectrometer 58 to analyze probe beam 26 as BRS 14, except that DUV 16 uses the reflective lens 33 instead of focusing lens 32. To operate DUV 16, the turret containing lenses 32/33 is rotated so that reflective lens 33 is aligned in probe beam 26. The reflective lens 33 is necessary because solid objective lenses cannot sufficiently focus the UV light onto the sample.

Broadband spectroscopic ellipsometry (BSE) is discussed in U.S. Pat. No. 5,877,859, issued Mar. 2, 1999, which is commonly owned by the present assignee and is incorporated herein by reference. BSE (18) includes a polarizer 70, focusing mirror 72, collimating mirror 74, rotating compensator 76, and analyzer 80. In operation, mirror 82 directs at least part of probe beam 26 to polarizer 70, which creates a known polarization state for the probe beam, preferably a linear polarization. Mirror 72 focuses the beam onto the sample surface at an oblique angle, ideally on the order of 70 degrees to the normal of the sample surface. Based upon well-known ellipsometric principles, the reflected beam will generally have a mixed linear and circular polarization state after interacting with the sample, based upon the composition and thickness of the sample's film 8 and substrate 6. The reflected beam is collimated by mirror 74, which directs the beam to the rotating compensator 76. Compensator 76 introduces a relative phase delay δ (phase retardation) between a pair of mutually orthogonal polarized optical beam components. Compensator 76 is rotated (continuously or stepped) about an axis substantially parallel to the propagation direction of the beam, preferably by an electric motor 78. Analyzer 80, preferably another linear polarizer, mixes the polarization states incident on it. By measuring the light transmitted by analyzer 80, the polarization state of the reflected probe beam can be determined. Mirror 84 directs the beam to spectrometer 58, which simultaneously measures the intensities of the different wavelengths of light in the reflected probe beam that pass through the compensator/analyzer combination. Processor 48 receives the output of the detector 66, and processes the intensity information measured by the detector 66 as a function of wavelength and as a function of the azimuth (rotational) angle of the compensator 76 about its axis of rotation, to solve the ellipsometric values .psi. and .DELTA. as described in U.S. Pat. No. 5,877,859. Detector/camera 86 is positioned above mirror 46, and can be used to view reflected beams off of the sample 4 for alignment and focus purposes.

System 400 also includes a narrow-band ellipsometer 2. Ellipsometer 2 includes a light source 90 that produces a quasi-monochromatic probe beam 106 having a known stable wavelength and stable intensity. Preferably, this result is achieved passively, where light source 90 generates a very stable output wavelength which does not vary over time (i.e. varies less than 1%). Examples of passively stable light sources are a helium-neon laser, or other gas discharge laser systems.

The beam 106 interacts with polarizer 92 to create a known polarization state. In the preferred embodiment, polarizer 92 is a linear polarizer made from a quartz Rochon prism, but in general the polarization does not necessarily have to be linear, nor even complete. Polarizer 92 can also be made from calcite. The azimuth angle of polarizer 92 is oriented so that the plane of the electric vector associated with the linearly polarized beam exiting from the polarizer 92 is at a known angle with respect to the plane of incidence (defined by the propagation direction of the beam 106 and the normal to the surface of sample 4). The azimuth angle is preferably selected to be on the order of 30 degrees because the sensitivity is optimized when the reflected intensities of the P and S polarized components are approximately balanced. It should be noted that polarizer 92 can be omitted if the light source 90 emits light with the desired known polarization state.

The beam 106 is focused onto the sample 4 by lens 94 at an oblique angle. The beam 106 is ideally incident on sample 4 at an angle on the order of 70 degrees to the normal of the sample surface because sensitivity to sample properties is maximized in the vicinity of the Brewster or pseudo-Brewster angle of a material. Based upon well-known ellipsometric principles, the reflected beam will generally have a mixed linear and circular polarization state after interacting with the sample, as compared to the linear polarization state of the incoming beam. Lens 96 collimates beam 106 after its reflection off of the sample 4.

The beam 106 then passes through the rotating compensator (retarder) 98, which introduces a relative phase delay .delta. (phase retardation) between a pair of mutually orthogonal polarized optical beam components. The amount of phase retardation is a function of the wavelength, the dispersion characteristics of the material used to form the compensator, and the thickness of the compensator. Compensator 98 is rotated (stepped or continuously) about an axis substantially parallel to the propagation direction of beam 106, preferably by an electric motor 100. Compensator 98 can be any conventional wave-plate compensator, for example those made of crystal quartz. The thickness and material of the compensator 98 are selected such that a desired phase retardation of the beam is induced. Beam 106 then interacts with analyzer 102, which serves to mix the polarization states incident on it. In this embodiment, analyzer 102 is another linear polarizer, preferably oriented at an azimuth angle of 45 degrees relative to the plane of incidence. The rotating compensator 98 changes the polarization state of the beam as it rotates.

Beam 106 then enters detector 104, which measures the intensity of the beam passing through the compensator/analyzer combination. The processor 48 processes the intensity information measured by the detector 104 to determine the polarization state of the light after interacting with the analyzer, and therefore the ellipsometric parameters of the sample. This information processing includes measuring beam intensity as a function of the azimuth (rotational) angle of the compensator about its axis of rotation.

The output of the processor can be supplied to a display 110 which can display parameters in various forms including two-dimensional maps. The output can be stored. The term stored or storage merely means that the data is in a form for future use, even if that use is immediate and the storage time is very short. This data can be transferred to another memory or onto a computer network. The output could be used in various feedback or feed forward control systems.

In another aspect, the design of the FEEs is performed by an optimization tool that accounts for measurement goals (e.g., measurement sensitivity and parameter correlations) and manufacturing design rules (e.g., design rules associated with the overall device fabrication process). In this manner, knowledge and constraints of the manufacturing process are incorporated into the optimization of the targets with FEEs.

The optimization of FEE targets can be done with the aid of a software modeling tool that analyzes the sensitivity and parameter correlation for the original structure and evaluates targets with FEEs that are compatible with the existing process. The software modeling tool may perform optimization with a cost function and/or constraints that utilize information about the fabrication process and the available system parameters (wavelengths, polarizations, angles of incidence, analyzer angles, etc.).

For example, structural characteristics may be identified based on a comparison between a measurement and a reference measurement. In some examples, the reference measurement may be an average of a number of measurements generated over a number of different locations of a specimen. In some other examples, the reference measurement may be a measurement associated with a reference wafer. The comparison between the measurement and the reference measurement, or reference measurements, may involve any number of comparison techniques known in the art.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD)), laser disc, optical disc, digital versatile disc (DVD), floppy disk and blu-ray disc where disks usually reproduce data magnetically, while discs reproduce data optically with lasers. Combinations of the above should also he included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
illuminating a specimen with an illumination light over a target area, the specimen including a first field enhancement element and a first structure of interest in the target area, wherein the first field enhancement element is disposed on the specimen to enhance a measurement of the structure of interest;
diffracting an amount of scattered light from a first target element at a plurality of angles in response to the illumination light, the first target element including the first field enhancement element and the first structure of interest, wherein the amount of scattered light interacts with the first structure of interest to generate an amount of measurement light;
detecting the amount of measurement light; and
determining a measurement parameter of the structure of interest based at least in part on the measurement light.

2. The method of claim 1, further comprising:
a second target element in the target area that includes a second field enhancement element and a second structure of interest, the second field enhancement element having the same shape and size as the first field enhancement element, wherein the second target element is spaced apart from the first target element by a first fixed spatial period in a first direction.

3. The method of claim 2, further comprising:
a third target element in the target area that includes a third field enhancement element and a third structure of interest, wherein the third target element is spaced apart from the first target element by a second fixed spatial period in a second direction not aligned with the first direction.

4. The method of claim 1, wherein the specimen is a semiconductor wafer having an amount of sacrificial die area, and wherein the first field enhancement element is located in the sacrificial die area.

5. The method of claim 1, further comprising:
a second target element that includes a second field enhancement element and a second structure of interest, the second field enhancement element having a different shape than the first field enhancement element, wherein the determining the measurement parameter of the structure of interest is based at least in part on the measurement light detected from the first target element and a second measurement light detected from the second target element.

6. The method of claim 1, wherein the first target element includes the first field enhancement element and a second field enhancement element having a different shape than the first field enhancement element.

7. The method of claim 1, wherein the first field enhancement element includes a first plurality of different material layers.

8. The method of claim 7, further comprising:
a second field enhancement element including a second plurality of different material layers.

9. The method of claim 1, wherein the field enhancement element is shaped to generate a resonance in the target element.

10. The method of claim 1, wherein a thin film material is disposed over the first field enhancement element, wherein the first field enhancement element includes a sharp feature to enhance concentration of an electric field in the film.

11. An apparatus comprising:
an illumination source operable to generate an amount of illumination light;
an optical element operable to receive the amount of illumination light from the illumination source and focus the amount of light on a target area of a specimen, the specimen including a first field enhancement element disposed on the specimen to enhance a measurement of at least one structure of interest, wherein a portion of the illumination light is incident on a first target element that includes the first field enhancement element and diffracts an amount of scattered light over a plurality of angles, and wherein the amount of scattered light interacts with the at least one structure of interest to generate an amount of measurement light;
a detector operable to generate at least one output signal in response to the amount of measurement light collected from the specimen; and
a computer configured to determine a measurement parameter associated with the structure of interest based at least in part on the at least one output signal.

12. The apparatus of claim 11, further comprising:
a second target element in the target area that includes a second field enhancement element and at least one structure of interest, the second field enhancement element having the same shape and size as the first field enhancement element, wherein the second target element is spaced apart from the first target element by a first fixed spatial period in a first direction.

13. The apparatus of claim 12, further comprising:
a third target element in the target area that includes a third field enhancement element and at least one structure of interest, wherein the third target element is spaced apart from the first target element by a second fixed spatial period in a second direction not aligned with the first direction.

14. The apparatus of claim 11, wherein the specimen is a semiconductor wafer having an amount of sacrificial die area, and wherein the first field enhancement element is located in the sacrificial die area.

15. The apparatus of claim 11, further comprising:
a second target element that includes a second field enhancement element and at least one structure of interest, the second field enhancement element having a different shape than the first field enhancement element, wherein the determining the measurement parameter of the at least one structure of interest is based at least in part on the measurement light detected from the first target element and a second measurement light detected from the second target element.

16. The method of claim 11, wherein the first target element includes the first field enhancement element and a second field enhancement element having a different shape than the first field enhancement element.

17. The apparatus of claim 11, wherein the first field enhancement element includes a first plurality of different material layers and a second field enhancement element includes a second plurality of different material layers.

18. The apparatus of claim 11, wherein the first field enhancement element is shaped to generate a resonance in the target element.

19. The apparatus of claim 11, wherein a thin film material is disposed over the first field enhancement element, the first field enhancement element having a sharp feature to enhance concentration of an electric field in the film.

20. A method comprising:
illuminating a first target element of a specimen with an illumination light, the first target element including a first field enhancement element and at least one structure of interest, wherein the first field enhancement element is disposed on the specimen to enhance a measurement of the at least one structure of interest;
diffracting a first amount of scattered light from the first target element at a plurality of angles in response to the illumination light, wherein the amount of scattered light interacts with the at least one structure of interest to generate a first amount of measurement light;
detecting the first amount of measurement light;
illuminating a second target element of a specimen with the illumination light, the second target element including a second field enhancement element and the at least one structure of interest, wherein the second field enhancement element is disposed on the specimen to enhance a measurement of the at least one structure of interest;
diffracting a second amount of scattered light from the second target element at a plurality of angles in response to the illumination light, wherein the second amount of scattered light interacts with the at least one structure of interest to generate a second amount of measurement light;
detecting the second amount of measurement light; and
determining a measurement parameter of the at least one structure of interest based at least in part on the first amount of measurement light and the second amount of measurement light.

* * * * *